(12) United States Patent
Murphy et al.

(10) Patent No.: US 10,799,305 B2
(45) Date of Patent: Oct. 13, 2020

(54) VARIABLE DRIVE FORCE APPARATUS AND METHOD FOR ROBOTIC CATHETER SYSTEM

(71) Applicant: Corindus, Inc., Waltham, MA (US)

(72) Inventors: John Murphy, North Reading, MA (US); Tal Wenderow, Newton, MA (US)

(73) Assignee: CORINDUS, INC., Waltham, MA (US)

( * ) Notice: Subject to any disclaimer, the term of this patent is extended or adjusted under 35 U.S.C. 154(b) by 207 days.

(21) Appl. No.: 15/667,294

(22) Filed: Aug. 2, 2017

(65) Prior Publication Data

US 2018/0125589 A1 May 10, 2018

Related U.S. Application Data

(63) Continuation of application No. 14/220,740, filed as application No. PCT/US2012/056336 on Sep. 20, 2012, now Pat. No. 9,750,576.

(60) Provisional application No. 61/537,030, filed on Sep. 20, 2011.

(51) Int. Cl.
*A61B 34/30* (2016.01)
*A61B 34/00* (2016.01)
*A61B 17/00* (2006.01)

(52) U.S. Cl.
CPC .............. *A61B 34/30* (2016.02); *A61B 34/25* (2016.02); *A61B 2017/00477* (2013.01); *A61B 2034/301* (2016.02)

(58) Field of Classification Search
CPC ... A61B 34/30; A61B 34/25; A61B 2034/301; A61B 2017/00477
See application file for complete search history.

(56) References Cited

U.S. PATENT DOCUMENTS

| | | | |
|---|---|---|---|
| 5,720,742 | A | 2/1998 | Zacharias |
| 5,821,920 | A | 10/1998 | Rosenberg et al. |
| 5,821,950 | A | 10/1998 | Rentschler et al. |
| 6,258,052 | B1 | 7/2001 | Milo |
| 6,264,630 | B1 | 7/2001 | Mickley et al. |
| 2006/0084945 | A1 | 4/2006 | Moll et al. |

(Continued)

FOREIGN PATENT DOCUMENTS

| WO | 2011046874 A1 | 4/2011 |
|---|---|---|
| WO | 2011109283 A1 | 9/2011 |

OTHER PUBLICATIONS

PCT International Preliminary Report on Patentability for PCT/US2012/056336, dated Apr. 3, 2014, 10 pages.

(Continued)

*Primary Examiner* — Dale Moyer

(74) *Attorney, Agent, or Firm* — Rathe Lindenbaum LLP

(57) ABSTRACT

A robotic system includes a bedside system comprising an axial drive mechanism and a rotational drive mechanism. An engagement mechanism engages and disengages a percutaneous device from at least one of the axial drive mechanism and rotational drive mechanism. A remote work station includes a user interface and a control system operatively coupled to the user interface. The control system is configured to communicate a control signal to the engagement mechanism to engage and disengage the percutaneous device from one of the axial drive mechanism and rotational drive mechanism.

20 Claims, 7 Drawing Sheets

(56) References Cited

U.S. PATENT DOCUMENTS

| | | | |
|---|---|---|---|
| 2007/0197939 A1* | 8/2007 | Wallace | A61B 5/6885 |
| | | | 600/587 |
| 2008/0027313 A1 | 1/2008 | Shachar | |
| 2008/0082109 A1 | 4/2008 | Moll et al. | |
| 2008/0319341 A1 | 12/2008 | Taylor et al. | |
| 2009/0138025 A1 | 5/2009 | Stahler et al. | |
| 2010/0069833 A1* | 3/2010 | Wenderow | A61M 25/0113 |
| | | | 604/95.01 |
| 2010/0076310 A1 | 3/2010 | Wenderow et al. | |
| 2012/0071895 A1* | 3/2012 | Stahler | A61B 6/12 |
| | | | 606/130 |
| 2013/0035537 A1* | 2/2013 | Wallace | A61B 34/30 |
| | | | 600/8 |
| 2018/0353250 A1* | 12/2018 | Fournier | A61M 25/0113 |

OTHER PUBLICATIONS

PCT Search Report and Written Opinion for PCT/US2012/056336, dated Jan. 23, 2013, 11 pages.

\* cited by examiner

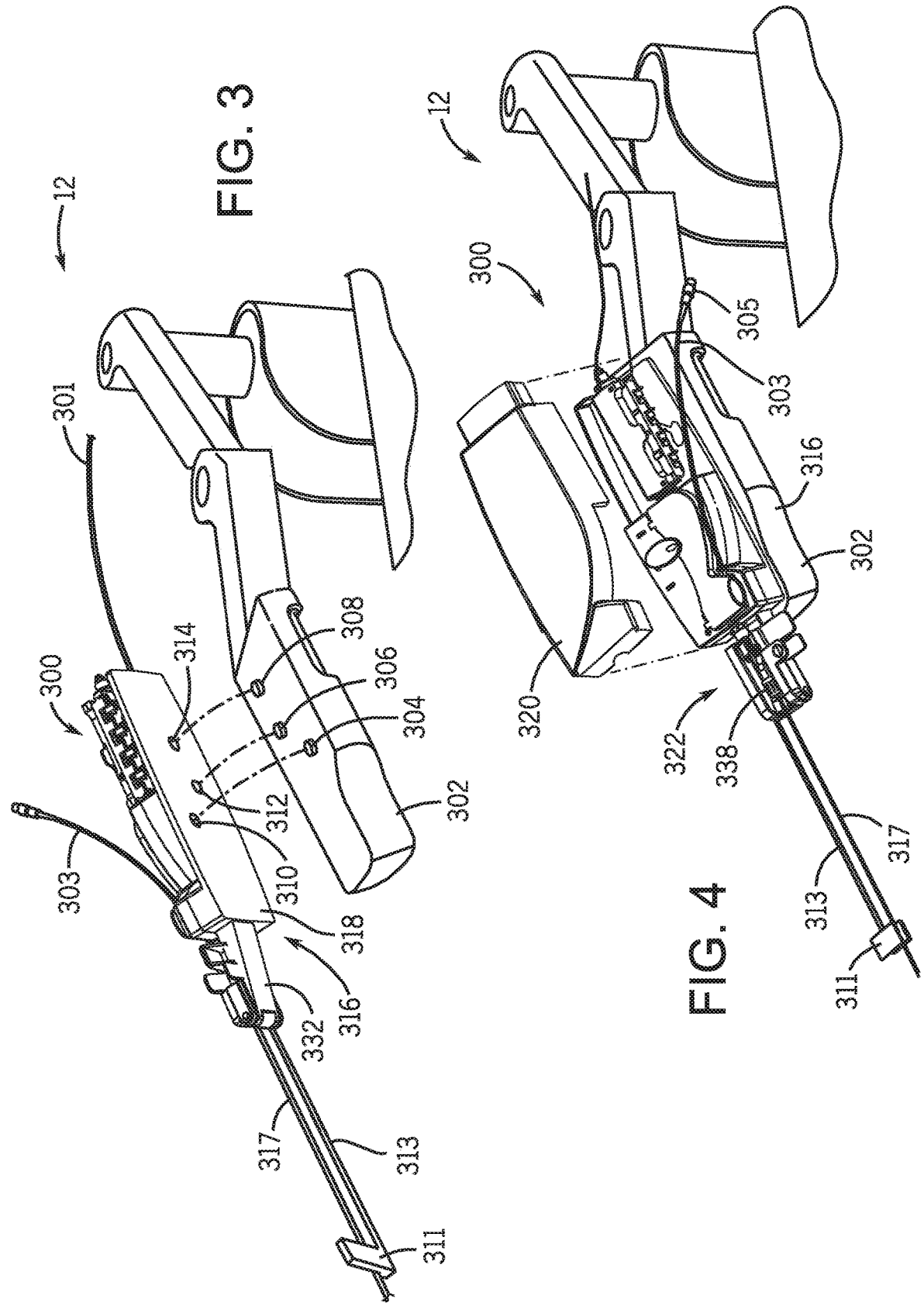

VARIABLE DRIVE FORCE APPARATUS AND METHOD FOR ROBOTIC CATHETER SYSTEM

CROSS-REFERENCE TO RELATED APPLICATIONS

This application is a continuation of U.S. patent application Ser. No. 14/220,740 which is a National Stage Entry of PCT/US2012/056336 entitled VARIABLE DRIVE FORCE APPARATUS AND METHOD FOR ROBOTIC CATHETER SYSTEM filed Sep. 20, 2012, which claims the benefit of the U.S. Provisional Application No. 61/537,030, filed Sep. 20, 2011, all of which are incorporated herein by reference in their entirety.

BACKGROUND OF THE INVENTION

The present invention relates generally to the field of catheter systems for performing diagnostic and/or intervention procedures. The present invention relates specifically to catheter systems including a mechanism for controlling and varying the driving force applied to a percutaneous device.

Vascular disease, and in particular cardiovascular disease, may be treated in a variety of ways. Surgery, such as cardiac bypass surgery, is one method for treating cardiovascular disease. However, under certain circumstances, vascular disease may be treated with a catheter based intervention procedure, such as angioplasty. Catheter based intervention procedures are generally considered less invasive than surgery. If a patient shows symptoms indicative of cardiovascular disease, an image of the patient's heart may be taken to aid in the diagnosis of the patient's disease and to determine an appropriate course of treatment. For certain disease types, such as atherosclerosis, the image of the patient's heart may show a lesion that is blocking one or more coronary arteries. Following the diagnostic procedure, the patient may undergo a catheter based intervention procedure. During one type of intervention procedure, a catheter is inserted into the patient's femoral artery and moved through the patient's arterial system until the catheter reaches the site of the lesion. In some procedures, the catheter is equipped with a balloon or a stent that when deployed at the site of a lesion allows for increased blood flow through the portion of the coronary artery that is affected by the lesion. In addition to cardiovascular disease, other diseases (e.g., hypertension, etc.) may be treated using catheterization procedures.

SUMMARY OF THE INVENTION

In one embodiment, a robotic system includes a bedside system comprising an axial drive mechanism and a rotational drive mechanism. An engagement mechanism engages and disengages a percutaneous device from at least one of the axial drive mechanism and rotational drive mechanism. A remote work station includes a user interface and a control system operatively coupled to the user interface. The control system is configured to communicate a control signal to the engagement mechanism to engage and disengage the percutaneous device from one of the axial drive mechanism and rotational drive mechanism.

In a further feature, the control system is configured to communicate a control signal to the engagement mechanism to disengage the rotational drive mechanism from the percutaneous device when a user provides an instruction through the user interface to the axial drive mechanism to axially translate the percutaneous device.

In a further feature, the control system is configured to communicate a control signal to the engagement mechanism to disengage the axial drive mechanism from the percutaneous device when a user provides an instruction through the user interface to the rotational drive mechanism to rotate the percutaneous device.

In a further feature, the control system is configured to communicate a control signal to the engagement mechanism to alternatively disengage the axial drive mechanism and rotational drive mechanism from the percutaneous device when a user provides an instruction through the user interface to both axially translate and rotate the percutaneous device.

In a further feature, the engagement mechanism engages and disengages the percutaneous device at least ten times per second.

In a further feature, the control system is configured to communicate a control signal to the engagement mechanism to disengage the rotational drive mechanism from the percutaneous device when a user provides an instruction through the user interface and control system to the axial drive mechanism to axially translate the percutaneous device where the percutaneous device is slipping relative to the axial drive mechanism.

In another feature, an axial sensor is configured to detect the axial translation of the percutaneous device and communicate a signal to the controller representative of the speed of the axial translation of the percutaneous device. The controller is configured to compare output of the axial sensor with the axial drive mechanism and determine whether the percutaneous device is slipping relative to the axial drive mechanism.

In a further feature, a rotational sensor is configured to detect the rotational speed of the percutaneous device and communicate a signal to the control system representative of the rotational speed of the percutaneous device. The control system is configured to compare the output of the rotational sensor with the rotational drive mechanism and determine whether the percutaneous device is rotationally slipping relative to the rotational translational drive mechanism.

In a further feature, the control system is configured to communicate a control signal to the engagement mechanism to disengage the axial drive mechanism from the percutaneous device when a user provides an instruction through the user interface and control system to the rotational drive mechanism to rotate the percutaneous device where the percutaneous device is slipping relative to the rotational drive mechanism.

In a further feature, the axial drive mechanism includes a drive wheel and roller defining axial engagement surfaces, the percutaneous device being engaged and disengaged between the drive wheel and roller, the engagement mechanism including a linear engagement mechanism configured to move drive wheel and roller toward and away from one another to respectively engage and disengage the percutaneous device.

In a further feature, the rotational drive mechanism includes a pair of rollers. The percutaneous device being engaged and disengaged between the rollers, the engagement mechanism including a rotational engagement mechanism configured to move the rollers toward and away from one another to respectively engage and disengage the percutaneous device.

In a further feature, the control system is configured to communicate a control signal to a motor operatively coupled to the drive wheel to reduce a rotational speed of the drive wheel when the control system detects linear slippage of the percutaneous device relative to the drive wheel until the percutaneous device is not slipping relative to the drive wheel.

In still a further feature, the control system is configured to communicate a control signal to the motor to increase the speed of the drive wheel when slippage is no longer detected.

In a further feature, the speed of the drive wheel is increased in a step wise function.

In a further feature, the control system is configured to communicate a control signal to a motor operatively coupled to the drive wheel to increase a rotational speed of the drive wheel when the control system detects linear slippage of the percutaneous device relative to the drive wheel until the percutaneous device is moving linearly at a required speed.

In a further feature, the axial engagement mechanism is configured to vary the distance between a rotational axis of the drive wheel and a rotational axis of the roller to vary the force applied to the percutaneous device in a direction perpendicular to the rotational axes of the drive wheel and roller.

Alternative exemplary embodiments relate to other features and combinations of features as may be generally recited in the claims.

In a further feature, the control system is configured to reduce the distance between the drive wheel and roller when the percutaneous device is slipping relative to the drive wheel.

In a further feature the percutaneous device is one of a guide wire, working catheter and a guide catheter.

In another embodiment, a method for controlling a percutaneous device, includes providing a bedside system comprising, an axial drive mechanism, a rotational drive mechanism, and an engagement mechanism to engage and disengage a percutaneous device from at least one of the axial drive mechanism and rotational drive mechanism; providing a remote work station comprising a user interface and control system operatively coupled to the user interface, and providing a control signal from the control system to the engagement mechanism engaging and disengaging the percutaneous device from one of the axial drive mechanism and rotational drive mechanism.

Another feature includes disengaging the percutaneous device from the rotational drive mechanism when the axial drive mechanism is axially driving the percutaneous device.

Another feature includes disengaging the percutaneous device from the axial drive mechanism when the rotational drive mechanism is rotationally driving the percutaneous device.

Another feature includes alternatively disengaging and engaging the percutaneous device from the axial drive mechanism and rotational drive mechanism.

Another feature includes sensing the axial movement of the percutaneous device and comparing the movement of the axial drive mechanism to determine if the percutaneous device is slipping relative to the axial drive mechanism.

Another feature includes reducing the speed of a drive motor in the axial drive mechanism until the percutaneous device is no longer slipping relative to the axial drive mechanism.

Another feature includes subsequently increasing the speed of a drive motor in the axial drive mechanism so long as the percutaneous device is no longer slipping relative to the axial drive mechanism.

Another feature includes increasing the speed of a drive motor in the axial drive mechanism until the percutaneous device is moving at a desired rate. The features noted above may be combined in a number of different combinations all of which are contemplated.

Alternative exemplary embodiments relate to other features and combinations of features as may be generally recited in the claims.

BRIEF DESCRIPTION OF THE DRAWINGS

This application will become more fully understood from the following detailed description, taken in conjunction with the accompanying figures, wherein like reference numerals refer to like elements in which:

FIG. 3 is a perspective view of a bedside system showing a cassette prior to being attached to a motor drive base according to an exemplary embodiment;

FIG. 4 is a perspective view of a bedside system showing the cassette of FIG. 3 following attachment to the motor drive base according to an exemplary embodiment;

DETAILED DESCRIPTION OF THE PREFERRED EMBODIMENTS

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

Figure 1:
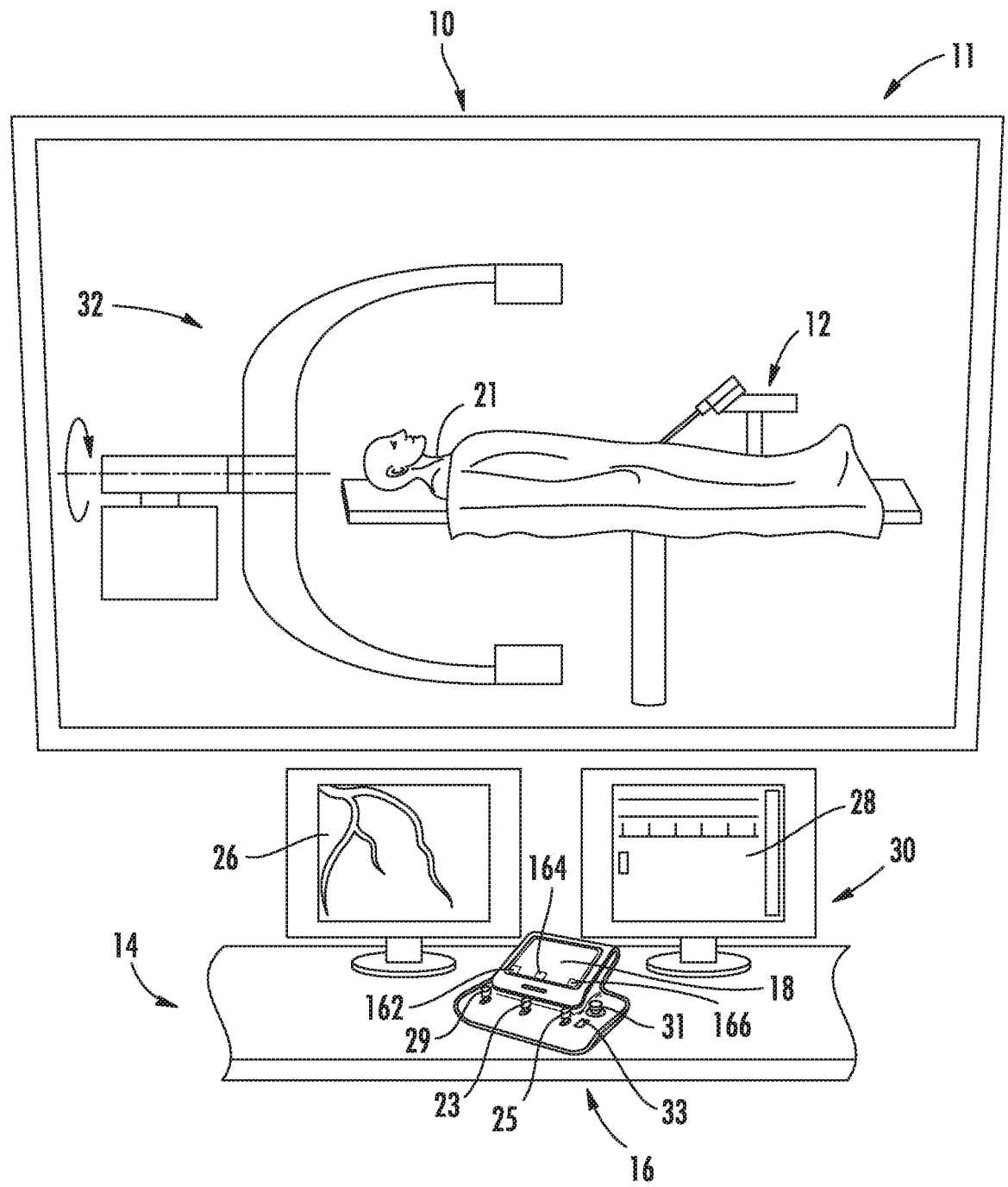
FIG. 1 is a perspective view of a catheter procedure system according to an exemplary embodiment.

Referring to FIG. 1, a catheter procedure system 10 is shown. Catheter procedure system 10 may be used to perform catheter based medical procedures (e.g., percutaneous intervention procedures). Percutaneous intervention procedures may include diagnostic catheterization procedures during which one or more catheters are used to aid in the diagnosis of a patient's disease. For example, during one embodiment of a catheter based diagnostic procedure, a contrast media is injected into one or more coronary arteries through a catheter and an image of the patient's heart is taken. Percutaneous intervention procedures may also include catheter based therapeutic procedures (e.g., balloon angioplasty, stent placement, treatment of peripheral vascular disease, etc.) during which a catheter is used to treat a disease. It should be noted, however, that one skilled in the art would recognize that, certain specific percutaneous intervention devices or components (e.g., type of guide wire, type of catheter, etc.) will be selected based on the type of procedure that is to be performed. Catheter procedure system 10 is capable of performing any number of catheter based medical procedures with minor adjustments to accommodate the specific percutaneous devices to be used in the procedure. In particular, while the embodiments of catheter procedure system 10 described herein are explained primarily in relation to the diagnosis and/or treatment of coronary disease, catheter procedure system 10 may be used to diagnose and/or treat any type of disease or condition amenable to diagnosis and/or treatment via a catheter based procedure.

Catheter procedure system 10 includes lab unit 11 and workstation 14. Catheter procedure system 10 includes a robotic catheter system, shown as bedside system 12, located within lab unit 11 adjacent patient 21. Generally, bedside system 12 may be equipped with the appropriate percutaneous devices (e.g., guide wires, guide catheters, working, catheters, catheter balloons, stents, diagnostic catheters, etc.) or other components (e.g., contrast media, medicine, etc.) to allow the user to perform a catheter based medical procedure. A robotic catheter system, such as bedside system 12, may be any system configured to allow a user to perform a catheter-based medical procedure via a robotic system by operating various controls such as the controls located at workstation 14. Bedside system 12 may include any number and/or combination of components to provide bedside system 12 with the functionality described herein. Various embodiments of bedside system 12 are described in detail in P.C.T. International Application No. PCT/US2009/042720, filed May 4, 2009, which is incorporated herein by reference in its entirety. Further, U.S. Patent Publication No. 2010/0076308 (U.S. patent application Ser. No. 12/626,516), U.S. Patent Publication No. 2010/0076310 (U.S. patent application Ser. No. 12/626,531), U.S. Patent Publication No. 2010/0069833 (U.S. patent application Ser. No. 12/626,503), and U.S. Patent Publication No. 2010/0076309 (U.S. patent application Ser. No. 12/626,525), which are continuation applications of P.C.T. International Application No. PCT/US2009/042720, are incorporated herein by reference in their entirety.

In one embodiment, bedside system 12 may be equipped to perform a catheter based diagnostic procedure, and in another embodiment, bedside system 12 may be equipped to perform a catheter based therapeutic procedure. Bedside system 12 may be equipped with one or more of a variety of catheters for the delivery of contrast media to the coronary arteries. In one embodiment, bedside system 12 may be equipped with a first catheter shaped to deliver contrast media to the coronary arteries on the left side of the heart, a second catheter shaped to deliver contrast media to the coronary arteries on the right side of the heart, and a third catheter shaped to deliver contrast media into the chambers of the heart. In other embodiments, bedside system 12 may be equipped with a guide catheter, a guide wire, and a working catheter (e.g., a balloon catheter, a stent delivery catheter, ablation catheter, etc.). In one embodiment, bedside system 12 may equipped with a working catheter that includes a secondary lumen that is threaded over the guide wire during a procedure. In another embodiment, bedside system 12 may be equipped with an over-the-wire working catheter that includes a central lumen that is threaded over the guide wire during a procedure. In another embodiment, bedside system 12 may be equipped with an intravascular ultrasound (IVUS) catheter. In another embodiment, any of the percutaneous devices of bedside system 12 may be equipped with positional sensors that indicate the position of the component within the body.

Bedside system 12 is in communication with workstation 14, allowing signals generated by the user inputs and control system of workstation 14 to be transmitted to bedside system 12 to control the various functions of beside system 12. Bedside system 12 also may provide feedback signals (e.g., operating conditions, warning signals, error codes, etc.) to workstation 14. Bedside system 12 may be connected to workstation 14 via a communication link 38 that may be a wireless connection, cable connectors, or any other means capable of allowing communication to occur between workstation 14 and beside system 12.

Workstation 14 includes a user interface 30. User interface 30 includes controls 16. Controls 16 allow the user to control bedside system 12 to perform a catheter based medical procedure. For example, controls 16 may be configured to cause bedside system 12 to perform various tasks using the various percutaneous devices with which bedside system 12 may be equipped (e.g., to advance, retract, or rotate a guide wire, advance, retract, or rotate a working catheter, advance, retract, or rotate a guide catheter, inflate or deflate a balloon located on a catheter, position and/or deploy a stent, inject contrast media into a catheter, inject medicine into a catheter, or to perform any other function that may be performed as part of a catheter based medical procedure, etc.).

In one embodiment, controls 16 include a touch screen 18, a dedicated guide catheter control 29, a dedicated guide wire control 23, and a dedicated working catheter control 25. In this embodiment, guide wire control 23 is a joystick configured to cause bedside system 12 to advance, retract, or rotate a guide wire, working catheter control 25 is a joystick configured to cause bedside system 12 to advance, retract, or rotate a working catheter, and guide catheter control 29 is a joystick configured to cause bedside system 12 to advance, retract, or rotate a guide catheter. In addition, touch screen 18 may display one or more icons (such as icons 162, 164, and 166) that control movement of one or more percutaneous devices via bedside system 12. Controls 16 may also include a balloon or stent control that is configured to inflate or deflate a balloon and/or a stent. Each of the controls may include one or more buttons, joysticks, touch screens, etc., that may be desirable to control the particular component to which the control is dedicated.

Controls 16 may include an emergency stop button 31 and a multiplier button 33. When emergency stop button 31 is pushed a relay is triggered to cut the power supply to bedside system 12. Multiplier button 33 acts to increase or decrease the speed at which the associated component is moved in response to a manipulation of guide catheter control 29, guide wire control 23, and working catheter control 25. For example, if operation of guide wire control 23 advances the guide wire at a rate of 1 mm/sec, pushing multiplier button 33 may cause operation of guide wire control 23 to advance the guide wire at a rate of 2 mm/sec. Multiplier button 33 may be a toggle allowing the multiplier effect to be toggled on and off. In another embodiment, multiplier button 33 must be held down by the user to increase the speed of a component during operation of controls 16.

User interface 30 may include a first monitor 26 and a second monitor 28. First monitor 26 and second monitor 28 may be configured to display information or patient specific data to the user located at workstation 14. For example, first monitor 26 and second monitor 28 may be configured to display image data (e.g., x-ray images, MRI images, CT images, ultrasound images, etc.), hemodynamic data (e.g., blood pressure, heart rate, etc.), patient record information (e.g., medical history, age, weight, etc.). In addition, first monitor 26 and second monitor 28 may be configured to display procedure specific information (e.g., duration of procedure, catheter or guide wire position, volume of medicine or contrast agent delivered, etc.). Monitor 26 and monitor 28 may be configured to display information regarding the position and/or bend of the distal tip of a steerable guide catheter. Further, monitor 26 and monitor 28 may be configured to display information to provide the functionalities associated with the various modules of controller 40 discussed below. In another embodiment, user interface 30 includes a single screen of sufficient size to display one or more of the display components and/or touch screen components discussed herein.

Catheter procedure system 10 also includes an imaging system 32 located within lab unit 11. Imaging system 32 may be any medical imaging system that may be used in conjunction with a catheter based medical procedure (e.g., non-digital x-ray, digital x-ray, CT, MM, ultrasound, etc.). In an exemplary embodiment, imaging system 32 is a digital x-ray imaging device that is in communication with workstation 14. As shown in FIG. 1, imaging system 32 may include a C-arm that allows imaging system 32 to partially or completely rotate around patient 21 in order to obtain images at different angular positions relative to patient 21 (e.g., sagital views, caudal views, cranio-caudal views, etc.).

Imaging system 32 is configured to take x-ray images of the appropriate area of patient 21 during a particular procedure. For example, imaging system 32 may be configured to take one or more x-ray images of the heart to diagnose a heart condition. Imaging system 32 may also be configured to take one or more x-ray images during a catheter based medical procedure (e.g., real-time images) to assist the user of workstation 14 to properly position a guide wire, guide catheter, working catheter, stent, etc. during the procedure. The image or images may be displayed on first monitor 26 and/or second monitor 28.

In addition, the user of workstation 14 may be able to control the angular position of imaging system 32 relative to the patient to obtain and display various views of the patient's heart on first monitor 26 and/or second monitor 28. Displaying different views at different portions of the procedure may aid the user of workstation 14 properly move and position the percutaneous devices within the 3D geometry of the patient's heart. In an exemplary embodiment, imaging system 32 may be any 3D imaging modality of the past, present, or future, such as an x-ray based computed tomography (CT) imaging device, a magnetic resonance imaging device, a 3D ultrasound imaging device, etc. In this embodiment, the image of the patient's heart that is displayed during a procedure may be a 3D image. In addition, controls 16 may also be configured to allow the user positioned at workstation 14 to control various functions of imaging system 32 (e.g., image capture, magnification, collimation, c-arm positioning, etc.).

Figure 2:
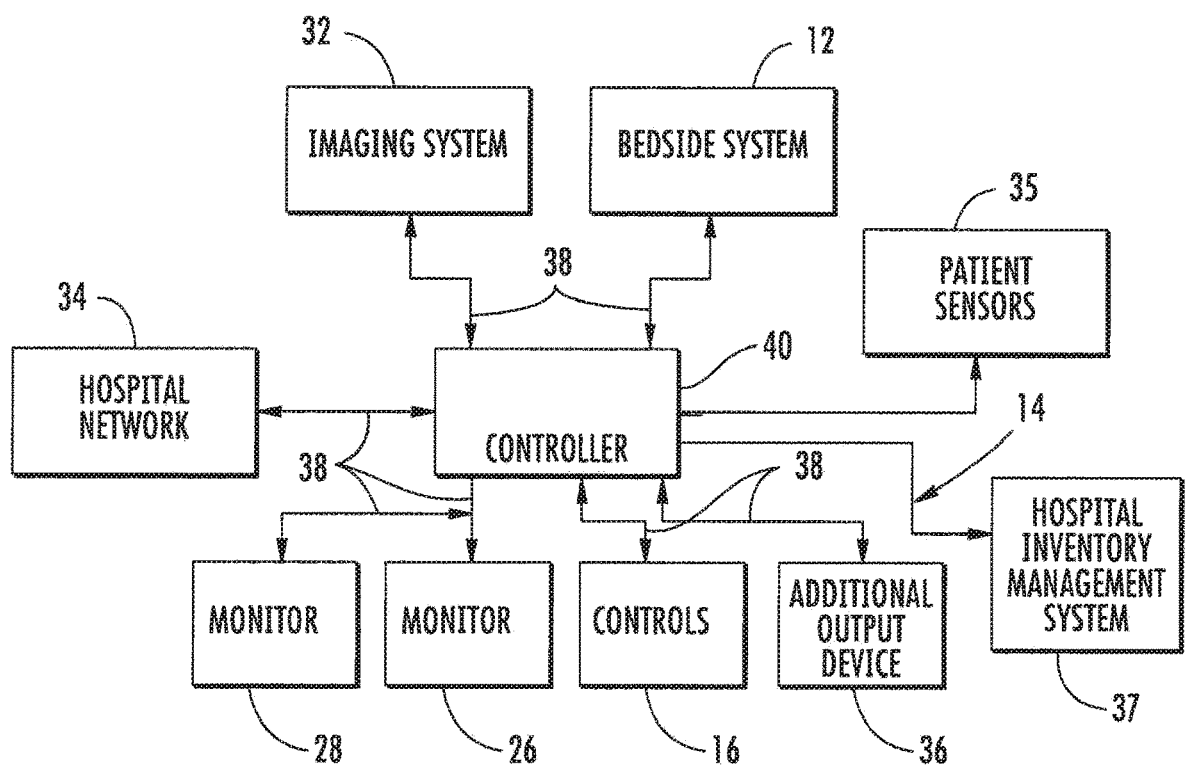
FIG. 2 is a block diagram of a catheter procedure system according to an exemplary embodiment.

Referring to FIG. 2, a block diagram of catheter procedure system 10 is shown according to an exemplary embodiment. Catheter procedure system 10 may include a control system, shown as controller 40. As shown in FIG. 2, controller 40 may be part of workstation 14. Controller 40 is in communication with one or more bedside systems 12, controls 16, monitors 26 and 28, imaging system 32, and patient sensors 35 (e.g., electrocardiogram ("ECG") devices, electroencephalogram ("EEG") devices, blood pressure monitors, temperature monitors, heart rate monitors, respiratory monitors, etc.). In addition, controller 40 may be in communication with a hospital data management system or hospital network 34, one or more additional output devices 36 (e.g., printer, disk drive, cd/dvd writer, etc.), and a hospital inventory management system 37.

Communication between the various components of catheter procedure system 10 may be accomplished via communication links 38. Communication links 38 may be dedicated wires or wireless connections. Communication links 38 may also represent communication over a network. Catheter procedure system 10 may be connected or configured to include any other systems and/or devices not explicitly shown. For example, catheter procedure system 10 may include IVUS systems, image processing engines, data storage and archive systems, automatic balloon and/or stent inflation systems, contrast media and/or medicine injection systems, medicine tracking and/or logging systems, user logs, encryption systems, systems to restrict access or use of catheter procedure system 10, robotic catheter systems of the past, present, or future, etc.

Referring to FIG. 3-6, an exemplary embodiment of bedside system 12 is shown that is configured to allow a user to advance, retract and rotate a guide wire and to advance and retract a working catheter by operating controls 16 located at workstation 14. In the embodiment shown, bedside system 12 includes a cassette 300 and a motor drive base 302. Cassette 300 is equipped with a guide wire 301 and with a working catheter 303 to allow a user to perform a catheterization procedure utilizing cassette 300. In this embodiment, cassette 300 is configured to be mounted to motor drive base 302. FIG. 3 shows a bottom perspective view of cassette 300 prior to mounting to motor drive base 302. Motor drive base 302 includes a first capstan 304, a second capstan 306, and a third capstan 308. Cassette 300 includes a first capstan socket 310, a second capstan socket 312, and a third capstan socket 314. Cassette 300 includes a housing 316, and housing 316 includes a base plate 318.

Each of the capstan sockets is configured to receive one of the capstans of motor drive base 302. In the embodiment shown, base plate 318 includes a hole or aperture aligned with each of the capstan sockets 310, 312, and 314 to allow each capstan to engage with the appropriate capstan socket. As discussed in more detail below, the engagement between the capstans and capstan sockets allows the transfer of energy (e.g., rotational movement) generated by one or more actuators (e.g., motors) located within motor drive base 302 to each of the drive mechanisms within cassette 300. In one embodiment, a single actuator provides energy to each of the drive mechanisms. In another embodiment, there is an actuator that drives capstan 304, an actuator that drives capstan 306, and an actuator that drives capstan 308. Further, the positioning of the capstans and capstan sockets helps the user to align cassette 300 relative to motor drive base 302 by allowing cassette 300 to be mounted to motor drive base 302 only when all three capstan sockets are aligned with the proper capstan.

In one embodiment, the motors that drive capstans 304, 306, and 308 are located within motor drive base 302. In another embodiment, the motors that drive capstans 304, 306, and 308 may be located outside of base 302 connected to cassette 300 via an appropriate transmission device (e.g., shaft, cable, etc.). In yet another embodiment, cassette 300 includes motors located within the housing of cassette 300. In another embodiment, cassette 300 does not include capstan sockets 310, 312, and 314, but includes an alternative mechanism for transferring energy (e.g., rotational motion) from an actuator external to the cassette to each of the cassette drive mechanisms. For example, rotational movement may be transferred to the drive mechanisms of cassette 300 via alternating or rotating magnets or magnetic fields located within motor drive base 302.

In the embodiment shown, cassette 300 also includes a guide catheter support 311 that supports guide catheter 317 at a position spaced from cassette 300. As shown, guide catheter support 311 is attached to cassette 300 by a rod 313. Rod 313 and guide catheter support 311 are strong enough to support guide catheter 317 without buckling. Guide catheter support 311 supports guide catheter 317 at a position spaced from the cassette, between the patient and the cassette to prevent buckling, bending, etc. of the portion of guide catheter 317 between the cassette and the patient.

Referring to FIG. 4, cassette 300 is shown mounted to motor drive base 302. As shown in FIG. 4, cassette 300 includes an outer cassette cover 320 that may be attached to housing 316. When attached to housing 316, outer cassette cover 320 is positioned over and covers each of the drive mechanisms of cassette 300. By covering the drive assemblies of cassette 300, outer cassette cover 320 acts to prevent accidental contact with the drive mechanisms of cassette 300 while in use.

Figure 5:
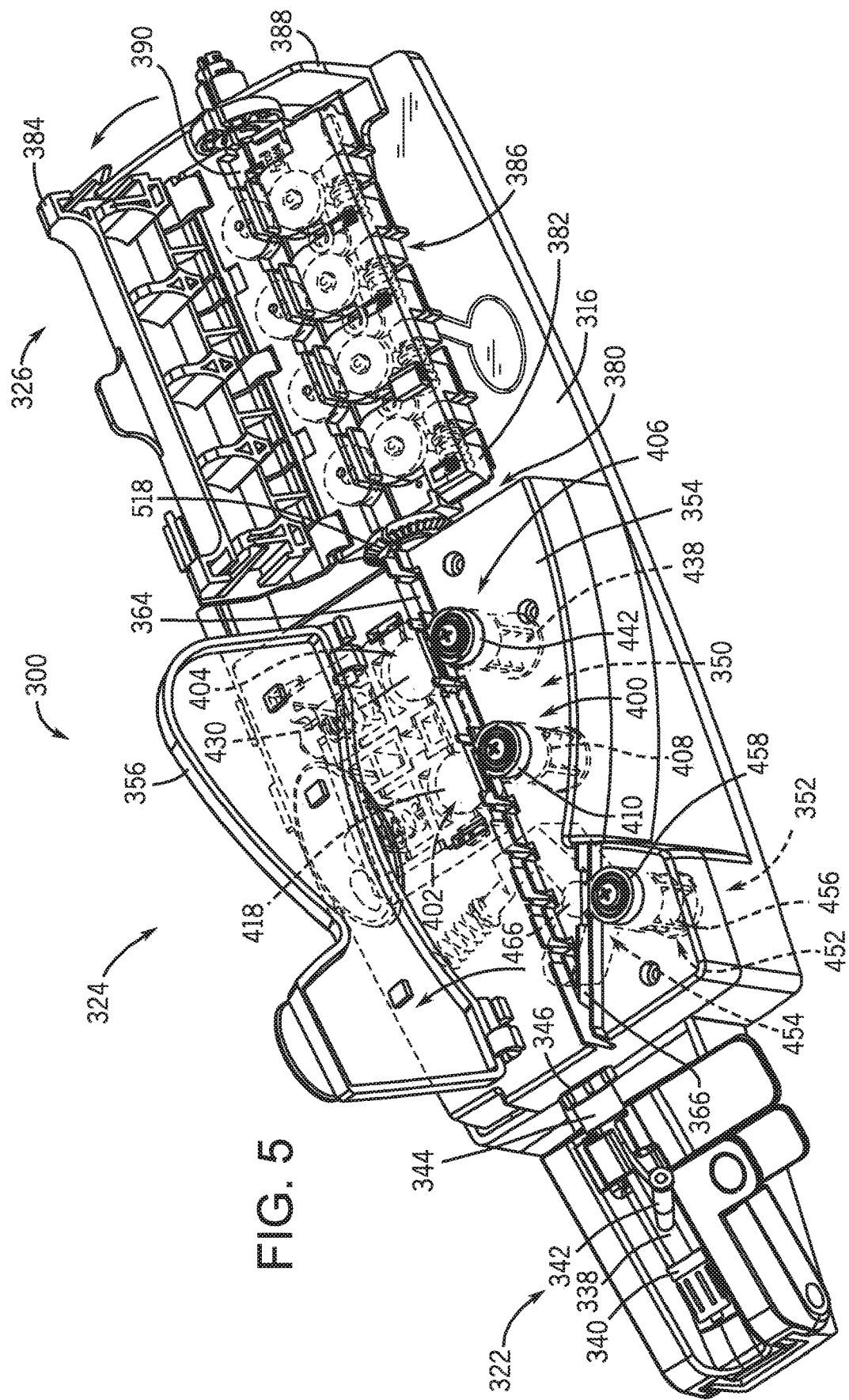
FIG. 5 is a perspective view of a cassette according to an exemplary embodiment.
Figure 6:
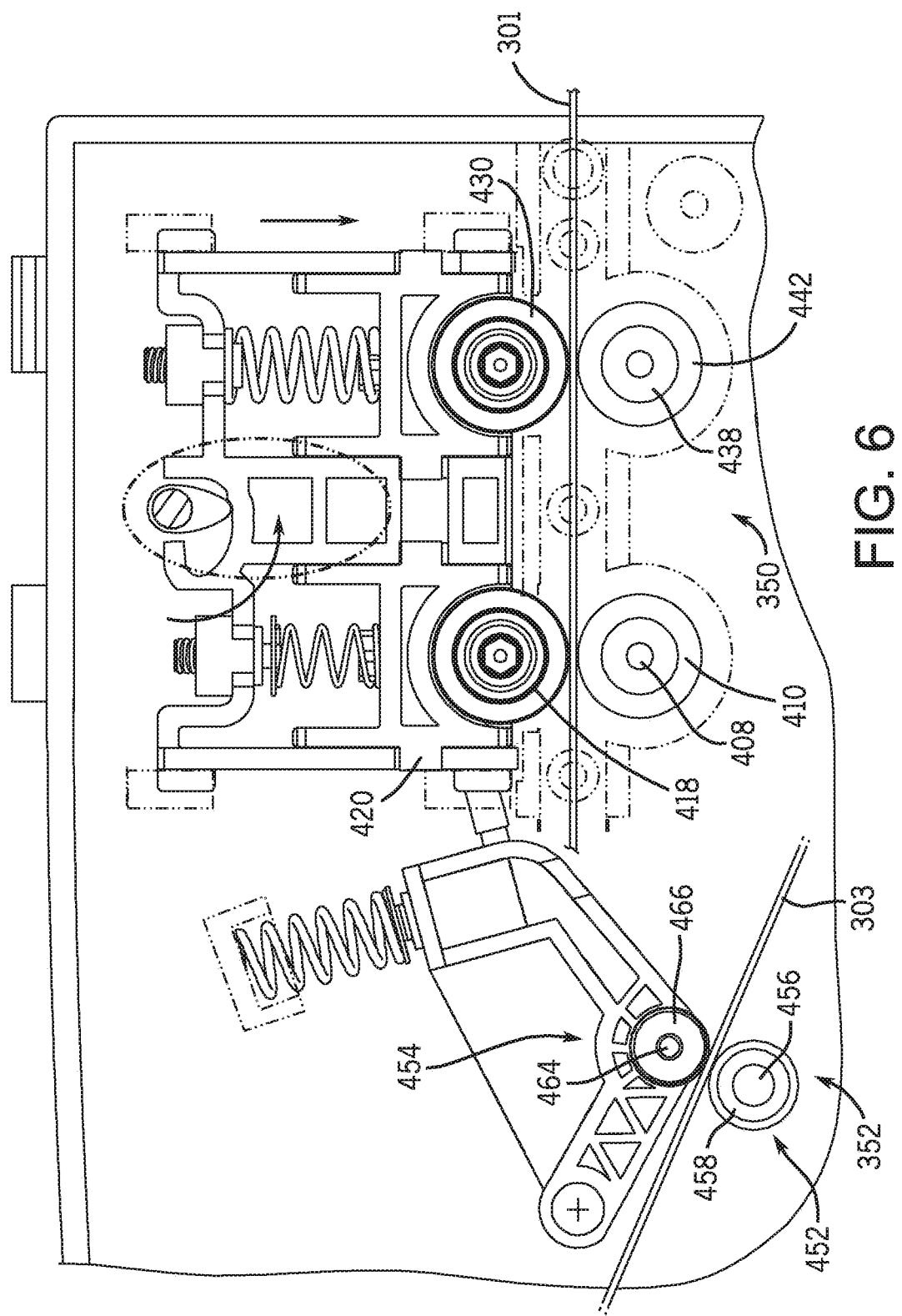
FIG. 6 is a top view showing an axial drive assembly of a cassette in the "engaged" position according to an exemplary embodiment.

Referring to FIG. 5, cassette 300 is shown in the "loading" configuration with outer cassette cover 320 removed. Cassette 300 includes a y-connector support assembly 322, an axial drive assembly 324, and a rotational drive assembly 326. Generally, the various portions of cassette 300 are placed in the loading configuration to allow the user to load or install a guide wire and/or working catheter into cassette 300. Cassette 300 includes a Y-connector 338 supported by y-connector support assembly 322. Y-connector 338 includes a first leg 340, a second leg 342, and a third leg 344. First leg 340 is configured to attach to a guide catheter such that the central lumen of the y-connector is in fluid communication with the central lumen of the guide catheter. Second leg 342 is angled away from the longitudinal axis of y-connector 338. Second leg 342 of y-connector 338 allows introduction of a contrast agent or medicine into the lumen of the guide catheter. A one way valve prohibits bodily fluid from exiting second leg 342. Third leg 344 extends away from the guide catheter toward axial drive assembly 324. In use, guide wire 301 and working catheter 303 are inserted into third leg 344 of y-connector 338 via opening 346 and may be advanced through y-connector 338 into the lumen of the guide catheter. The third leg also includes a one way valve that permits insertion and removal of the working catheter and guide wire but prohibits bodily fluids from exiting third leg 344.

Cassette 300 also includes an axial drive assembly 324. Axial drive assembly 324 includes a first axial drive mechanism, shown as guide wire axial drive mechanism 350, and a second axial drive mechanism, shown as working catheter axial drive mechanism 352. Axial drive assembly 324 also includes a top deck 354 and a cover 356.

Generally, in use, a guide wire, such as guide wire 301, is placed within guide wire channel 364 formed in top deck 354, and guide wire axial drive mechanism 350 is configured to releasably engage and drive (e.g., to impart motion to) guide wire 301 along its longitudinal axis. In this manner, guide wire axial drive mechanism 350 provides for advancement and/or retraction of guide wire 301. In use, a working catheter, such as working catheter 303, is placed within working catheter channel 366 formed in top deck 354, and working catheter axial drive mechanism 352 is configured to releasably engage and drive (e.g., to impart motion to) working catheter 303 along its longitudinal axis. In this manner, working catheter axial drive mechanism 352 provides for advancement and/or retraction of working catheter 303.

Cassette 300 also includes a rotational drive assembly 326. Rotational drive assembly 326 includes a rotational drive mechanism, shown as guide wire rotational drive mechanism 380, a cover 384, and a journal 388. Guide wire rotational drive mechanism 380 includes a chassis 382 and an engagement structure 386. Rotational drive assembly 326 is configured to cause guide wire 301 to rotate about its longitudinal axis. Engagement structure 386 is configured to releasably engage guide wire 301 and to apply sufficient force to guide wire 301 such that guide wire 301 is allowed to rotate about its longitudinal axis while permitting guide wire 301 to be moved axially by guide wire axial drive mechanism 350. In the embodiment shown, rotational drive assembly 326 is supported within housing 316 such that rotation drive assembly 326 is permitted to rotate within and relative to housing 316. In use, the guide wire, such as guide wire 301, is received within guide wire channel 390 defined in chassis 382, and engagement structure 386 engages guide wire 301 applying sufficient force to guide wire 301 such that the rotation of rotational drive assembly 326 causes guide wire 301 to rotate about its longitudinal axis as rotational drive assembly 326 rotates. Rotational drive mechanism 380 includes a rotation bevel gear 518 that is configured to be coupled to capstan 308 of motor drive base 302 such that rotational drive assembly 326 rotates in response to rotation of capstan 308.

FIG. 5 shows cover 356 and cover 384 in the open positions. When cover 356 and cover 384 are in the open positions, guide wire axial drive mechanism 350, working catheter axial drive mechanism 352, and rotational drive mechanism 380 are exposed allowing the user to load cassette 300 with a guide wire and working catheter. Once the guide wire and working catheter are positioned within guide wire channel 364, guide wire channel 390 and working catheter channel 366, respectively, engagement surfaces of guide wire axial drive mechanism 350, rotational drive mechanism 380 and working catheter axial drive mechanism 352 are brought into engagement with the guide wire and working catheter respectively. With the engagement structures of the respective drive mechanisms engaged, a user may operate controls 16 at workstation 14 to cause movement the guide wire and the working catheter.

Guide wire axial drive mechanism 350 includes a drive element 400, a first roller assembly 402, a second roller assembly 404, and a guide wire axial motion sensor assembly, shown as encoder assembly 406 (first roller assembly 402 and second roller assembly 404 are shown in broken lines in FIG. 5). Drive element 400 includes a drive shaft 408 and a drive wheel 410. Drive shaft 408 is configured to engage second capstan 306 of motor drive base 302 such that drive shaft 408 and drive wheel 410 rotate in response to rotation of second capstan 306. First roller assembly 402 includes an idler wheel or roller 418. Second roller assembly 404 includes an idler wheel or roller 430, and encoder assembly 406 includes shaft 438, idler wheel or roller 442 and a magnetic coupling located at the lower end of shaft 438.

Drive wheel 410 includes an outer or engagement surface, and roller 418 includes an outer or engagement surface. Generally, when guide wire axial drive mechanism 350 is placed in the "use" or "engaged" position (shown in FIG. 6), guide wire 301 is positioned between drive wheel 410 and roller 418 such that the outer surface of drive wheel 410 and the outer surface of roller 418 engage the guide wire. In this embodiment, the outer surfaces of drive wheel 410 and roller 418 define a pair of engagement surfaces. The force applied to guide wire 301 by drive wheel 410 and roller 418 is such that drive wheel 410 is able to impart axial motion to guide wire 301 in response to the rotation of drive shaft 408 caused by rotation of second capstan 306. This axial motion allows a user to advance and/or retract a guide wire via manipulation of controls 16 located at workstation 14. Roller 418 is rotatably mounted within wheel housing 420 and rotates freely as drive wheel 410 rotates to drive guide wire 301.

In the "engaged" position, guide wire 301 is positioned between roller 430 and roller 442 such that the outer surfaces of roller 430 and of roller 442 engage the guide wire. In this embodiment, the outer surfaces of roller 430 and of roller 442 define a pair of engagement surfaces. Both rollers 430 and 442 are mounted to rotate freely as drive wheel 410 imparts axial motion to guide wire 301, and the force applied to guide wire 301 by the outer surfaces of roller 430 and of roller 442 is such that drive wheel 410 is able to pull guide wire 301 past roller 430 and 442. In this way, the pair of non-active or idle rollers 430 and 442 help support guide wire 301 and maintain alignment of guide wire 301 along the longitudinal axis of cassette 300.

Encoder assembly 406 includes magnetic coupling at the base of shaft 438 that engages a magnetic encoder located within motor drive base 302. The magnetic encoder is configured to measure an aspect (e.g., speed, position, acceleration, etc.) of axial movement of the guide wire. As roller 442 rotates, shaft 438 rotates causing the magnetic coupling to rotate. The rotation of magnetic coupling causes rotation of the magnetic encoder within motor drive base 302. Because rotation of roller 442 is related to the axial movement of guide wire 301, the magnetic encoder within motor drive base 302 is able to provide a measurement of the amount of axial movement experienced by guide wire 301 during a procedure. This information may be used for a variety of purposes. For example, this information may be displayed to a user at workstation 14, may be used in a calculation of or estimated position of the guide wire within the vascular system of a patient, may trigger an alert or alarm indicating a problem with guide wire advancement, etc. Further, as discussed below, this information may be used by procedure control module 98 to calculate and to vary the amount of force or torque being applied to guide wire 301 by drive wheel 410.

Axial drive assembly 324 also includes working catheter axial drive mechanism 352. Working catheter axial drive mechanism 352 includes a drive element 452 and a working catheter axial motion sensor assembly, shown as working catheter encoder assembly 454. Drive element 452 includes a drive shaft 456 and a drive wheel 458. Drive shaft 456 is configured to engage first capstan 304 of motor drive base 302 such that drive shaft 456 and drive wheel 458 rotate in response to rotation of first capstan 304. Encoder assembly 454 includes shaft 464 and a roller 466, and a magnetic coupling located at the lower end of shaft 464.

Drive wheel 458 includes an outer surface and roller 466 includes an outer surface. When working catheter axial drive mechanism 352 is in the "engaged" position, working catheter 303 is positioned between drive wheel 458 and roller 466, such that outer surfaces of drive wheel 458 and roller 466 engage working catheter 303. In this embodiment, the outer surfaces of drive wheel 458 and roller 466 define a pair of engagement surfaces. The force applied to working catheter 303 by the outer surfaces of drive wheel 458 and roller 466 is such that drive wheel 458 is able to impart axial motion to the working catheter in response to the rotation of drive shaft 456 caused by rotation of first capstan 304. This axial motion allows a user to advance and/or retract a working catheter via manipulation of controls 16 located at workstation 14. Roller 466 is rotatably mounted to shaft 464 and rotates freely as drive wheel 458 rotates to drive the working catheter.

Encoder assembly 454 includes a magnetic coupling located at the lower end of shaft 464 that engages a magnetic encoder located within motor drive base 302. The magnetic encoder is configured to measure an aspect (e.g., speed, position, acceleration, etc.) of axial movement of the working catheter. As roller 466 rotates, shaft 464 rotates causing the magnetic coupling to rotate. The rotation of the magnetic coupling causes rotation of the magnetic encoder within motor drive base 302. Because rotation of roller 466 is related to the axial movement of working catheter 303, the magnetic encoder within motor drive base 302 is able to provide a measurement of the amount of axial movement experienced by the working catheter during a procedure. This information may be used for a variety of purposes. For example, this information may be displayed to a user at workstation 14, may be used in a calculation of or estimated position of the working catheter within the vascular system of a patient, may trigger an alert or alarm indicating a problem with working catheter advancement, etc. Further, as discussed below in relation to the guide wire motor, this information may be used by procedure control module 98 to calculate and to vary the amount of force or torque being applied to working catheter 303 by drive wheel 458.

Figure 7:
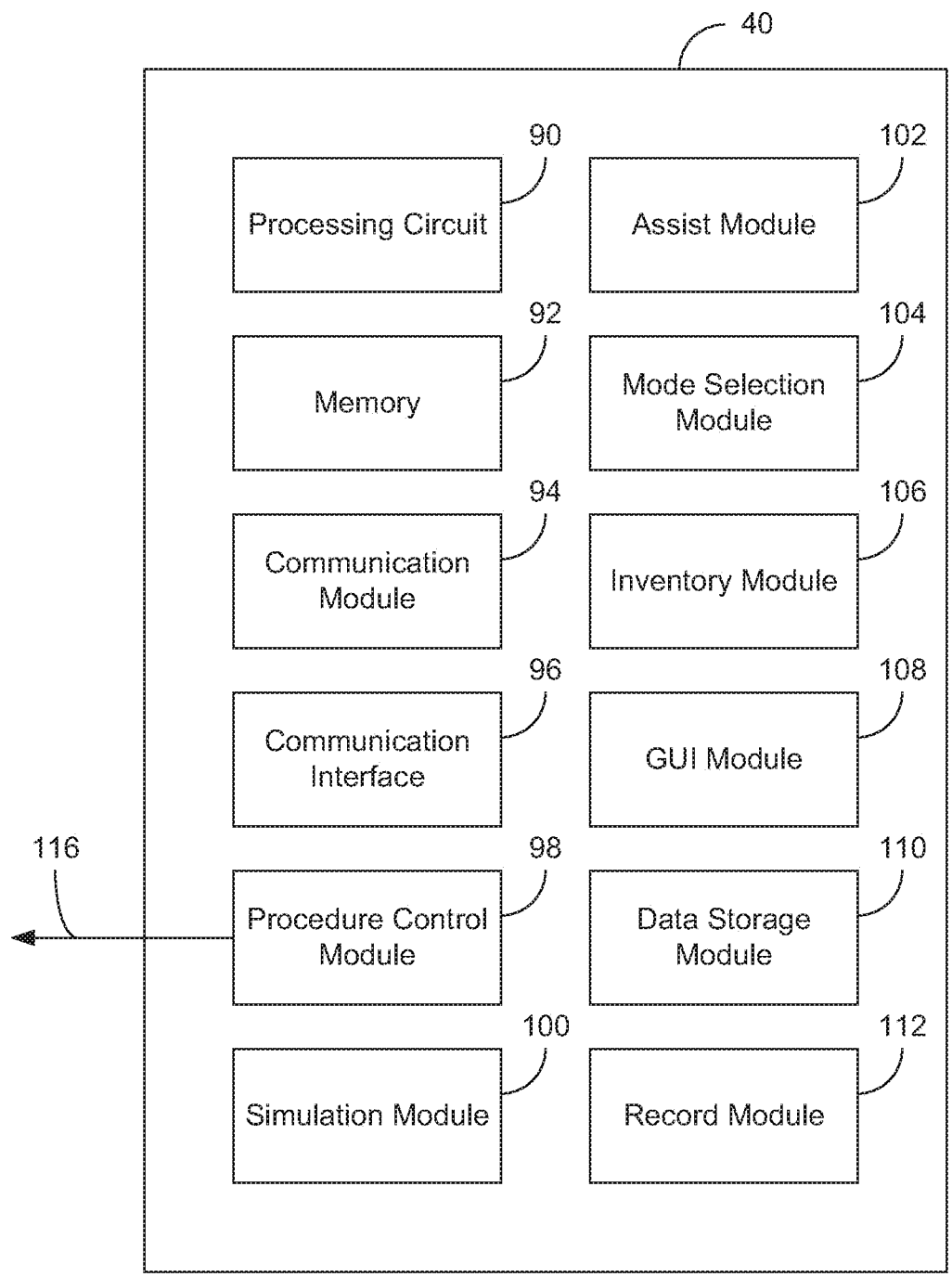
FIG. 7 is a block diagram of a controller for controlling a robotic catheter system according to an exemplary embodiment.

Referring to FIG. 7, a block diagram of controller 40 is shown according to an exemplary embodiment. Controller 40 may generally be an electronic control unit suitable to provide catheter procedure system 10 with the various functionalities described herein. For example, controller 40 may be an embedded system, a dedicated circuit, a general purpose system programmed with the functionality described herein, etc. Controller 40 includes a processing circuit 90, memory 92, communication module or subsystem 94, communication interface 96, procedure control module or subsystem 98, simulation module or subsystem 100, assist control module or subsystem 102, mode selection module or subsystem 104, inventory module or subsystem 106, GUI module or subsystem 108, data storage module or subsystem 110, and record module or subsystem 112.

Processing circuit 90 may be a general purpose processor, an application specific processor (ASIC), a circuit containing one or more processing components, a group of distributed processing components, a group of distributed computers configured for processing, etc., configured provide the functionality of module or subsystem components 94, 98-112. Memory 92 (e.g., memory unit, memory device, storage device, etc.) may be one or more devices for storing data and/or computer code for completing and/or facilitating the various processes described in the present disclosure. Memory 92 may include volatile memory and/or non-volatile memory. Memory 92 may include database components, object code components, script components, and/or any other type of information structure for supporting the various activities described in the present disclosure.

According to an exemplary embodiment, any distributed and/or local memory device of the past, present, or future may be utilized with the systems and methods of this disclosure. According to an exemplary embodiment, memory 92 is communicably connected to processing circuit 90 and module components 94, 98-112 (e.g., via a circuit or any other wired, wireless, or network connection) and includes computer code for executing one or more processes described herein. A single memory unit may include a variety of individual memory devices, chips, disks, and/or other storage structures or systems.

Module or subsystem components 94, 98-112 may be computer code (e.g., object code, program code, compiled code, script code, executable code, or any combination thereof), hardware, software, or any combination thereof, for conducting each module's respective functions. Module components 94, 98-112 may be stored in memory 92, or in one or more local, distributed, and/or remote memory units configured to be in communication with processing circuit 90 or another suitable processing system.

Communication interface 96 includes one or more component for communicably coupling controller 40 to the other components of catheter procedure system 10 via communication links 38. Communication interface 96 may include one or more jacks or other hardware for physically coupling communication links 38 to controller 40, an analog to digital converter, a digital to analog converter, signal processing circuitry, and/or other suitable components. Communication interface 96 may include hardware configured to connect controller 40 with the other components of catheter procedure system 10 via wireless connections. Communication module 94 is configured to support the communication activities of controller 40 (e.g., negotiating connections, communication via standard or proprietary protocols, etc.).

Data storage module 110 is configured to support the storage and retrieval of information by controller 40. In one embodiment, data storage module 110 is a database for storing patient specific data, including image data. In another embodiment, data storage module 110 may be located on hospital network 34. Data storage module 110 and/or communication module 94 may also be configured to import and/or export patient specific data from hospital network 34 for use by controller 40.

Controller 40 also includes simulation module or subsystem 100, assist module or subsystem 102, mode selection module or subsystem 104, inventory module or subsystem 106, GUI module or subsystem 108, data storage module or subsystem 110, and record module or subsystem 112. Generally, simulation module 100 is configured to run a simulated catheterization procedure based upon stored vascular image data and also based upon a user's manipulation of controls 16. Generally, assist module 102 is configured to provide information to the user located at workstation 14 during a real and/or simulated catheterization procedure to assist the user with the performance of the procedure. Specific embodiments of controller 40, including specific embodiments of simulation module 100, and assist module 102, are described in detail in P.C.T. International Application No. PCT/US2009/055318, filed Aug. 28, 2009, which is incorporated herein by reference in its entirety. Other specific embodiments of controller 40, including specific embodiments of GUI module 108, are described in P.C.T. International Application No. PCT/US2009/055320, filed Aug. 28, 2009, which is incorporated herein by reference in its entirety.

Figure 8:
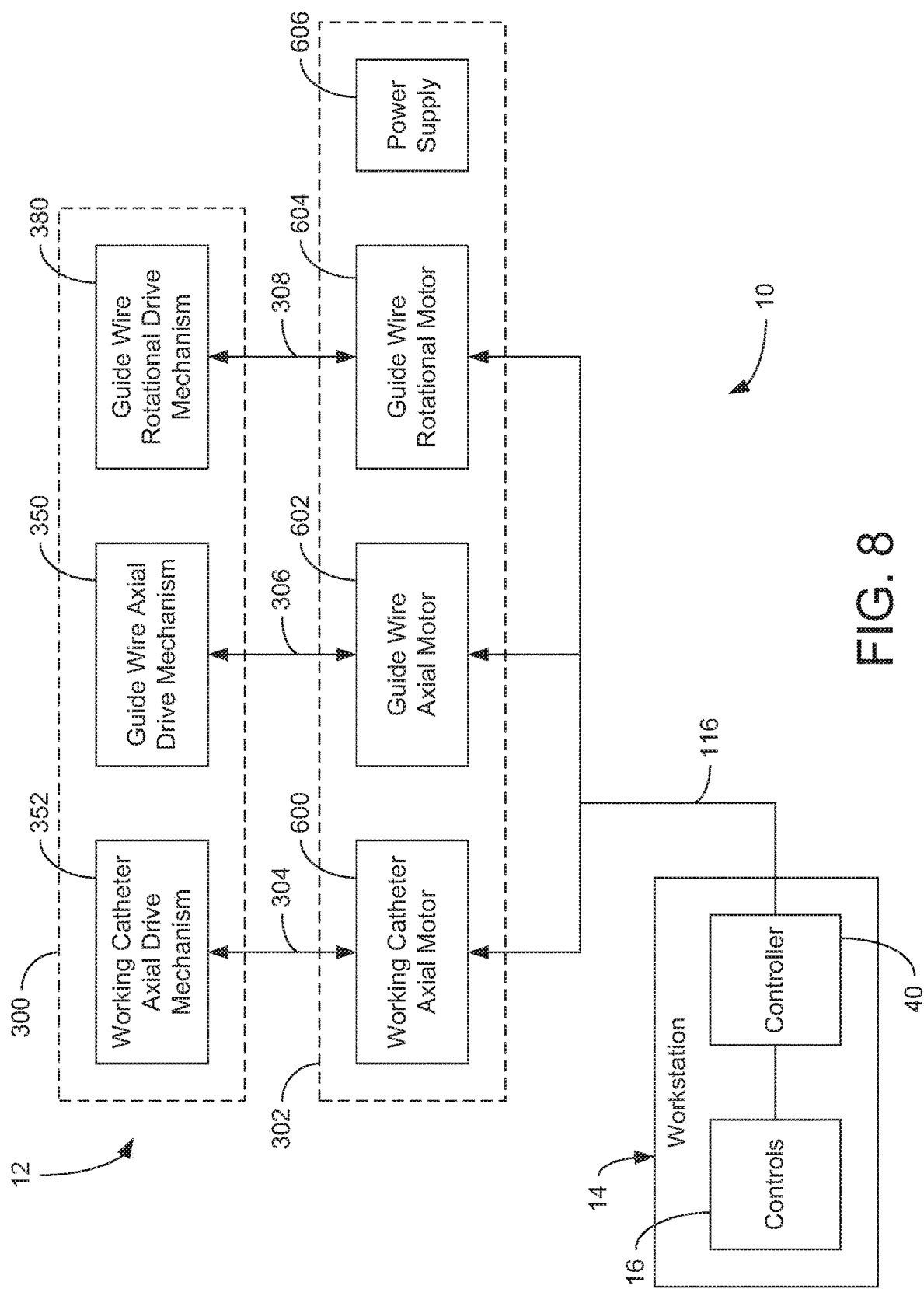
FIG. 8 is a block diagram of a catheter procedure system showing motors located within a motor drive base according to an exemplary embodiment.

Controller 40 also includes a procedure control module 98 configured to support the control of bedside system 12 during a catheter based medical procedure. Procedure control module 98 allows the user to operate bedside system 12 by manipulating controls 16. In various embodiments, procedure control module 98 is configured to generate one or more control signals 116 based upon the user's manipulation of controls 16 and, some embodiments, also based various data and information available to procedure control module 98. As shown in FIG. 8, control signals 116 generated by procedure control module 98 are communicated from controller 40 to the actuators or motors of bedside system 12. In response to control signals 116, the motors of bedside system 12 drive the drive mechanisms of cassette 300 (e.g., guide wire axial drive mechanism 350, working catheter axial drive mechanism 352, guide wire rotational drive mechanism 380, etc.) to cause movement of the guide wire or working catheter in accordance with the manipulation of controls 16 by the user. Procedure control module 98 may also cause data appropriate for a particular procedure to be displayed on monitors 26 and 28. Procedure control module 98 may also cause various icons (e.g., icons 162, 164, 166, etc.) to be displayed on touch screen 18 that the user may interact with to control the use of bedside system 12.

Referring to FIG. 8, a block diagram of catheter procedure system 10 is shown according to an exemplary embodiment. In the exemplary embodiment of FIG. 8, motor drive base 302 includes working catheter axial drive motor 600, guide wire axial drive motor 602, a guide wire rotational drive motor 604, and a power supply 606. Working catheter axial drive motor 600 drives capstan 304, guide wire axial drive motor 602 drives capstan 306 and guide wire rotational drive motor 604 drives capstan 308 to cause movement of working catheter 303 and guide wire 301 as discussed above. Motors 600, 602 and 604 are in communication with controller 40 such that control signals 116 may be received by motors 600, 602 and 604. Motors 600, 602 and 604 respond to control signals 116 by varying the rotation of capstans 304, 306 and 308 thereby varying the movement of working catheter 303 and guide wire 301 caused by drive mechanisms 352, 350 and 380. As shown, motor drive base 302 also includes a power supply 606 that may be, for example, a battery, the AC building power supply, etc.

In various embodiments, procedure control module 98 and guide wire axial drive motor 602 may be configured to provide for variability and control of the force applied to guide wire 301 by drive wheel 410 during advancement and retraction of guide wire 301. Variability and control of the force applied to guide wire 301 may be desirable for various reasons including, providing improved ability to traverse a partial occlusion or chronic total occlusion (collectively referred to as "CTO"), etc. In various embodiments, variability and control of the force applied to guide wire 301 is achieved by varying the current and/or voltage supplied to guide wire axial drive motor 602 from power supply 606. This control of guide wire axial drive motor 602 acts to vary the rotational speed and/or torque that guide wire axial drive motor 602 imparts to guide wire 301 via capstan 306 and drive wheel 410. In some embodiments, variation of current and/or voltage supplied to guide wire axial drive motor 602 from power supply 606 (and the corresponding variation in the rotational speed and/or torque that guide wire axial drive motor 602 imparts to guide wire 301) occurs in response to control signals 116 generated by procedure control module 98. As discussed in more detail below, control signals 116 may be based upon a user input (e.g., the user's operation of controls 16) and based upon a second input (e.g., other information or data available to procedure control module 98), and the actuator may provide torque to a percutaneous device (e.g., the guide wire) via a drive mechanism (as discussed above) in response to the control signal. As discussed below, procedure control module 98 is described as being configured to control, limit, vary, etc. the torque provided an actuator, such as guide wire axial drive motor 602, based on various inputs (e.g., information, data, operating conditions, etc.) and/or based upon user inputs received by a user interface (e.g., controls 16). It should be understood that, in one embodiment, the functionalities provided by control module 98 discussed below are provided by generating control signals 116 based upon the various inputs, and the control signals 116 are transmitted or communicated to an actuator (e.g., guide wire actuator 602). In this embodiment, the actuator then provides or generates a torque to a drive mechanism in response to the control signal.

During some intervention procedures, it is necessary that the guide wire traverse a partial or total occlusion of the coronary arteries. During these procedures, the guide wire must be advanced with enough force such that the guide wire pushes through the occlusion. However once the guide wire is through the occlusion it may be desirable to reduce the amount of torque the motor provides to drive the guide wire. Thus, in various embodiment, guide wire axial drive motor 602 is a motor having torque and speed characteristics such that it provides increased torque during traversal of the occlusion. For example, in one embodiment, guide wire axial drive motor 602 is configured to deliver sufficient torque via its output shaft such that the force imparted to guide wire 301 is great enough to allow guide wire 301 to traverse a total occlusion. In another embodiment, guide wire axial drive motor 602 is configured such that the maximum torque that may be delivered via its output shaft is such that the force imparted to guide wire 301 is not sufficient to traverse the occlusion. In another embodiment, guide wire axial drive motor 602 is selected to have a relatively low maximum output shaft speed (i.e., the no-load speed of the motor) to prevent sudden unwanted acceleration of guide wire 301. For example, the output speed of the motor shaft may be varied so as to not provide sufficient force to traverse the occlusion. This lower force may be useful when navigating the guide wire to the occlusion, or CTO. In one embodiment, the torque applied by the motor to the wheels driving the guide wire may be varied to maintain a constant rotational speed of the wheels driving the guide wire. In one embodiment a user may reduce the speed of the guide wire as the tip of the guide wire is about to fully traverse the lesion or CTO. Additionally, a user may reverse the direction of the guide wire upon fully traversing a lesion or CTO to remove any buckling in the guide wire that may have occurred prior to fully traversing the lesion or CTO. This potential unwanted acceleration of guide wire 301 can be minimized by selecting a guide wire axial drive motor 602 with a low maximum output shaft speed or with a controller that controls the speed to constant speed at a given input by the operator. For example if the operator moves a joy stick a certain distance from a neutral position, the speed will remain constant even if the torque is modified for a portion of the travel distance of the guide wire. In one embodiment, the speed of the guide wire may be kept constant, and the torque is varied by moving the joy stick from the neutral position. In this embodiment, as the joy stick is moved further from its neutral position increased torque is provided to the wheels driving the guide wire. As a guide wire is inhibited from moving forward due to frictional forces and/or a CTO, increased torque may be needed from the drive to move the guide wire forward. In one implementation a user may select to move the guide wire or rotate the guide wire at a constant speed while using the joy stick to vary the torque applied to the mechanisms used to linearly and rotating move the guide wire. A user may set the speed of the linear drive or the rotation drive for a certain time or distance be set by controls 16 at workstation 14. The joy stick in this mode then may be used to vary the torque applied to the drive mechanisms, allowing the user to modify the torque during a procedure. For example it may be desirable to increase the torque during navigation of a lesion or CTO and then to reduce the torque once the guide wire or working catheter has fully traversed the lesion or CTO. Alternatively, the speed is controlled by the joy stick and the controller adjusts the motor torque to obtain the speed required by the user.

In other embodiments, procedure control module 98 is configured to control the voltage and/or current supplied to guide wire axial drive motor 602 by power supply 606 in order to control and vary the force applied to guide wire 301 by drive wheel 410. In one embodiment, procedure control module 98 is configured to limit the maximum speed and maximum torque supplied by guide wire axial drive motor 602 based upon the current location of the tip of the guide wire within the patient's vascular system. Thus, in this embodiment, control signal 116 generated by procedure control module 98 may be based upon information related to the location of the tip of the guide wire within the patient and based upon the user's operation of controls 16. For example, procedure control module 98 may be configured such that the maximum speed and/or maximum torque supplied by guide wire axial drive motor 602 is set higher when the tip of the guide wire is located with the large arteries (e.g., aorta, femoral artery, etc.) and the maximum speed and/or maximum torque supplied by guide wire axial drive motor 602 is set lower when the tip of the guide wire is located with the smaller arteries (e.g., coronary arteries, etc.). In such embodiments, procedure control module 98 may be configured to determine the information related to the location of the tip of the guide wire in various way. For example, procedure control module 98 may prompt the user to input the current location of the tip of the guide wire via controls 16 (e.g., touch screen 18), location of the guide wire tip may be determined by image processing of images captured via imaging system 32, or the location may be determined via the distance information captured by a guide wire axial motion sensor assembly, such as encoder assembly 406, discussed above.

In another embodiment, procedure control module 98 is configured to limit the maximum speed and/or maximum torque supplied by guide wire axial drive motor 602 based upon the type of movement being performed by the guide wire. Thus, in one embodiment, control signal 116 generated by procedure control module 98 may be based upon information related to the direction of movement of the guide wire and based upon the user's operation of controls 16. For example, procedure control module 98 may be configured such that the maximum torque and/or speed supplied by guide wire axial drive motor 602 is set lower when the guide wire is being advanced and the maximum torque and/or speed supplied by the guide wire axial drive motor 602 is set higher when the guide wire is being retracted. This arrangement may be desirable because the risk of blood vessel perforation is lower when the guide wire is being retracted.

In other embodiments, procedure control module 98 may be configured to control the torque and speed supplied by guide wire axial drive motor 602 to assist in traversal of an occlusion such as a CTO. Thus, in one embodiment, control signal 116 generated by procedure control module 98 may be based upon information related to whether the tip of the percutaneous device is traversing an occluded portion of a vessel of the patient's vascular system and based upon the user's operation of controls 16. For example, procedure control module 98 may be configured such that the maximum torque supplied by guide wire axial drive motor 602 is set higher and the maximum speed supplied by guide wire axial drive motor 602 is set lower during traversal of a CTO. In this embodiment, controls 16 (e.g., touch screen 18) may include a button that the user selects when occlusion or CTO traversal is about to start thereby activating the occlusion or CTO traversal limits discussed above. In other embodiments, procedure control module 98 may determine that occlusion or CTO traversal is occurring by identifying the position of the guide wire relative to the occlusion or CTO from image information captured by imaging system 32. In another embodiment, procedure control module 98 may be configured to determine the extent of occlusion or CTO traversal that has occurred (i.e., how far through the occlusion or CTO the guide wire has traveled), and to control the torque and speed supplied by guide wire axial drive motor 602 based on the extent of occlusion or CTO traversal. For example, procedure control module 98 may be configured to decrease the torque supplied by guide wire axial drive motor 602 as the guide wire nears the end of the occlusion or CTO. In one such embodiment, the extent of occlusion or CTO traversal by the guide wire is determined from image information captured by imaging system 32.

In another embodiment, procedure control module 98 is configured to limit the maximum torque supplied by guide wire axial drive motor 602 such that the force imparted to guide wire 301 is low enough that guide wire 301 is capable of navigating through the blood vessels needed during a procedure at a proper force level. In one such embodiment, procedure control module 98 is configured with a set or non-variable maximum torque threshold such that the torque supplied by guide wire axial drive motor 602 remains below the threshold under all operating conditions. In this embodiment, the set or non-variable maximum torque threshold is selected such that the force applied to the guide wire is optimized for the type of blood vessel to be traversed during a particular procedure.

In another embodiment, procedure control module 98 is configured with a variable maximum torque threshold that is determined based upon various data or information accessible by procedure control module 98. In this embodiment, the torque supplied by guide wire axial drive motor 602 remains below the variable threshold during the procedure. In one such embodiment, the variable maximum torque threshold is determined from image data captured by imaging system 32. Thus, in this embodiment the maximum torque threshold may be determined based upon the thickness of the blood vessel walls at a certain location identified from the image data, and procedure control module 98 is configured to utilize the determined torque threshold to limit the maximum allowable torque of guide wire axial drive motor 602 as the guide wire traverses that portion of the blood vessel. In another embodiment, the maximum torque threshold utilized by procedure control module 98 is based upon the characteristics of the particular guide wire being used. For example, the maximum torque threshold may be set higher for a larger diameter guide wire than for a smaller diameter guide wire.

In another embodiment, procedure control module 98 may be configured to allow the user to set the maximum torque and maximum speed supplied by guide wire axial drive motor 602. In one embodiment, procedure control module 98 may display a button on touch screen 18 prompting the user to set the maximum torque and maximum speed. In another embodiment, controls 16 may include a set of controls (e.g., dials, sliders, etc.) allowing the user to set the maximum torque and maximum speed supplied by guide wire axial drive motor 602. In various embodiments, the user may be able to adjust the maximum torque and maximum speed as desired throughout the procedure.

In one embodiment, bedside system 12 may include a sensor configured to determine the amount of force applied to guide wire 301 by guide wire axial drive motor 602 as guide wire axial drive mechanism 350 advances and retracts the guide wire. In another embodiment, procedure control module 98 may be configured to determine the amount of force applied to guide wire 301 by guide wire axial drive motor 602 as guide wire axial drive mechanism 350 advances and retracts the guide wire by monitoring the operating state of guide wire axial drive motor 602. In one embodiment, procedure control module 98 is configured to display information related to determined amount of force to the user via a display device, such as monitors 26 and 28. For example, the display may be a bar display that fills in as force increase or a dial display with a needle that indicates the determined force. The display may also provide an indication of the force that would result in blood vessel perforation during the procedure. This indication may be an approximation based on location of the guide wire (e.g., in the aorta, in the coronary arteries, etc.) or this indication may be calculated from the image information of the patient's vascular system.

In various embodiments, procedure control module 98 and working catheter axial drive motor 600 may be configured to provide for variability and control of the force applied to working catheter 303 by drive wheel 458 during advancement and retraction of working catheter 303. Variability and control of the force applied to working catheter 303 may be desirable for various reasons including, lowering the risk of blood vessel perforation, providing improved ability to traverse a partial occlusion or chronic total occlusion (CTO), etc. It should be noted that, while the above disclosure related to primarily to variable control of force and speed imparted to a guide wire by guide wire axial drive motor 602, the same variable force and speed concepts may be applied to working catheter axial drive motor 600.

In one embodiment, guide wire 301 is translated axially by axial drive assembly 324 and rotational drive assembly 326. When both axial drive assembly 324 and rotational drive assembly are actively engaged with guide wire 302 a force is applied to the guide wire by both axial drive assembly 324 and rotational drive assembly 326. As discussed above, guide wire rotational drive mechanism 380 includes a chassis 382 and an engagement structure 386. Rotational drive assembly 326 is configured to cause guide wire 301 to rotate about its longitudinal axis. Engagement structure 386 is configured to releasably engage guide wire 301 and to apply sufficient force to guide wire 301 such that guide wire 301 is allowed to rotate about its longitudinal axis while permitting guide wire 301 to be moved axially by guide wire axial drive mechanism 350. However, the force required by the drive wheels 410 of the axial drive assembly to overcome the frictional force applied by the engagement structure of the 386 is greater than the force that would be required if the axial drive assembly were not so engaged. As a result a greater force is applied to the drive wheels and idler wheels of the axial drive mechanism. Similarly, the force required to securely engage guide wire 302 in the rotational drive mechanism to overcome the friction applied by the axial drive assembly is greater than if the axial drive assembly were not engaged.

Controller 40 may include instructions to selectively disengage the drive wheels of the axial drive assembly from the guide wire when the rotational drive mechanism is actively rotating the guide wire. Similarly, controller 40 may include instructions to selectively disengage the engagement structure of the rotational drive assembly from guide wire the when the axial drive assembly is actively engaged. This selective disengagement reduces the pressure applied to the guide wire thereby requiring less force to overcome the frictional force of the non-engaged drive mechanism. Similarly, when a user provides instructions to both rotate and axially drive the guide wire, controller 40 may include instructions to alternatively engage and disengage the rotational drive mechanism and the axial drive mechanism. If the instructions are provide rapidly, such as greater than 10 times per second, or 20 or more times per second such that impact will not be perceptible to a physician operating the system and will provide greater control of the rotational and axial drive assemblies as the frictional force of the other drive assembly will be significantly reduced and/or eliminated.

In addition to employing the rapid engage and disengage system to alternatingly engage and disengage the rotational and axial drive mechanisms when both rotational and axial drive mechanisms are in use. The engage and disengage feature may be used on each of the axial drive and rotational drive mechanisms. For example, in order to provide greater traction of the drive wheels 410 and idler wheels 418 the force applied to the drive wheels 410 may be rapidly and repeatedly increased and decreased to minimize slipping of the guide wire relative to the drive wheels 410. In one embodiment both drive wheels 410 are rapidly and repeatedly engaged and disengaged by controller 40 without the need for the physician or operator to repeatedly and rapidly turn a switch on and off. In another embodiment each pair of drive wheel 410 and idler wheel 418 may alternatively engage and disengage so that only one pair of drive wheel 410 and idler wheel 418 are engaged at one time. In another embodiment, if a sensor detects one idler wheel 410 is rotating more slowly than the other idler wheel, controller 40 may automatically provide instructions to disengage and reengage the idler wheel that is slipping to improve contact and engagement. Alternatively, controller 40 may reduce the speed and/or force of the non-drive wheel 410 associated with the non-slipping idler wheel until both idler wheels are rotating together and/or reduce the speed and/or force of both drive wheels.

In another embodiment, the force applied between the drive wheels and respective idler wheels maybe varied, so that the pinch force may be varied. Where the pinch force may be varied it may not be necessary to completely disengage the drive wheels and idler wheels or engagement surfaces of the rotational drive assembly, but rather it may be sufficient to reduce and increase the pinch force to achieve the desired result of enhanced control. By reducing the force of the drive wheel against the idler wheels or by reducing the force between the engagement surfaces in the rotational drive assembly, the deformation of the drive wheel surface and engagement surface is reduced thereby providing enhanced repeatable performance to the system.

In a further embodiment, controller 40 may provide instructions to adjust the speed and/or force between the drive wheel and idler wheel to decrease and/or increase the speed. A step function or a ramp function of increased speed and/or pressure between the drive wheel and idler wheels will provide enhanced control of the guide wire. In one embodiment, using a joy stick or other input device, a user may move the joy stick from its neutral position to request that a guide wire move a certain speed. If the actual speed of the guide wire being driven or rated is less than the speed requested by the user as a result of slippage of the guide wire with respect to the wheels, the controller may increase the speed of the wheels until the actual linear or rotational speed of the guide wire is equal to the speed requested by the user.

Further modifications and alternative embodiments of various aspects of the invention will be apparent to those skilled in the art in view of this description. Accordingly, this description is to be construed as illustrative only. The construction and arrangements of the robotic catheter device, as shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. A robotic system comprising:
    a bedside system comprising:
        an axial drive mechanism;
        a rotational drive mechanism; and
        an engagement mechanism to engage and disengage a percutaneous device from the axial drive mechanism and rotational drive mechanism; and
    a remote work station comprising:
        a user interface; and
        a control system operatively coupled to the user interface, the control system configured to communicate a control signal to the engagement mechanism to repeatedly engage and disengage the percutaneous device from one of the axial drive mechanism and rotational drive mechanism.

2. The robotic system of claim 1, wherein the control system is configured to communicate a control signal to the engagement mechanism to disengage the rotational drive mechanism from the percutaneous device when a user provides an instruction through the user interface to the axial drive mechanism to axially translate the percutaneous device.

3. The robotic system of claim 2, wherein the control system is configured to communicate a control signal to the engagement mechanism to disengage the axial drive mechanism from the percutaneous device when a user provides an instruction through the user interface to the rotational drive mechanism to rotate the percutaneous device.

4. The robotic system of claim 1, wherein the control system is configured to communicate a control signal to the engagement mechanism to repeatedly engage and disengage the axial drive mechanism from the percutaneous device when a user provides an instruction through the user interface to both axially translate and rotate the percutaneous device.

5. The robotic system of claim 4, wherein the engagement mechanism engages and disengages the percutaneous device at least ten times per second.

6. The robotic system of claim 5, further including an axial sensor configured to detect the axial translation of the percutaneous device and communicate a signal to the controller representative of the speed of the axial translation of the percutaneous device, the controller configured to compare output of the axial sensor with the axial drive mechanism and determine whether the percutaneous device is slipping relative to the axial drive mechanism.

7. The robotic system of claim 6, wherein the control system is configured to communicate a control signal to the engagement mechanism to disengage the rotational drive mechanism from the percutaneous device when a user provides an instruction through the user interface and control system to the axial drive mechanism to axially translate the percutaneous device where the percutaneous device is slipping relative to the axial drive mechanism.

8. The robotic system of claim 7, further including a rotational sensor configured to detect the rotational speed of the percutaneous device and communicate a signal to the control system representative of the rotational speed of the percutaneous device, the control system configured to compare output of the rotational sensor with the rotational drive mechanism and determine whether the percutaneous device is rotationally slipping relative to the rotational translational drive mechanism.

9. The robotic system of claim 8, wherein the control system is configured to communicate a control signal to the engagement mechanism to disengage the axial drive mechanism from the percutaneous device when a user provides an instruction through the user interface and control system to the rotational drive mechanism to rotate the percutaneous device where the percutaneous device is slipping relative to the rotational drive mechanism.

10. The robotic system of claim 1, further including an axial sensor configured to detect the axial translation of the percutaneous device and communicate a signal to the control system representative of the speed of the axial translation of the percutaneous device, the control system configured to compare output of the axial sensor with the axial drive mechanism and determine whether the percutaneous device is slipping relative to the axial drive mechanism.

11. The robotic system of claim 10, wherein the control system is configured to communicate a control signal to the engagement mechanism to disengage the rotational drive mechanism from the percutaneous device when a user provides an instruction through the user interface and control system to the axial drive mechanism to axially translate the percutaneous device where the percutaneous device is slipping relative to the axial drive mechanism.

12. The robotic system of claim 11, further including a rotational sensor configured to detect the rotational speed of the percutaneous device and communicate a signal to the control system representative of the rotational speed of the percutaneous device, the control system configured to compare output of the rotational sensor with the rotational drive mechanism and determine whether the percutaneous device is rotationally slipping relative to the rotational axial drive mechanism.

13. The robotic system of claim 12, wherein the control system is configured to communicate a control signal to the engagement mechanism to disengage the axial drive mechanism from the percutaneous device when a user provides an instruction through the user interface and control system to the rotational drive mechanism to rotate the percutaneous device where the percutaneous device is slipping relative to the rotational drive mechanism.

14. The robotic system of claim 1, wherein the percutaneous device is one of a guide wire, working catheter and a guide catheter.

15. A method for controlling a percutaneous device, comprising;
providing a bedside system comprising, an axial drive mechanism, a rotational drive mechanism, and an engagement mechanism to engage and disengage a percutaneous device from at least one of the axial drive mechanism and rotational drive mechanism;
providing a remote work station comprising a user interface and control system operatively coupled to the user interface, and
providing a control signal from the control system to the engagement mechanism repeatedly engaging and disengaging the percutaneous device from one of the axial drive mechanism and rotational drive mechanism,
wherein the control signal to the engagement mechanism is a signal to:
disengage the rotational drive mechanism from the percutaneous device responsive to an instruction from a user to the axial drive mechanism to axially translate the percutaneous device where the percutaneous device is determined to be slipping relative to the axial drive mechanism; or
disengage the axial drive mechanism from the percutaneous device responsive to an instruction from the user to the rotational drive mechanism to rotate the percutaneous device where the percutaneous device is determined to be slipping relative to the rotational drive mechanism.

16. The method of claim 15, including;
disengaging the percutaneous device from the rotational drive mechanism when the axial drive mechanism is axially driving the percutaneous device.

17. The method of claim 15, including;
disengaging the percutaneous device from the axial drive mechanism when the rotational drive mechanism is rotationally driving the percutaneous device.

18. The method of claim 15, including;
alternatively disengaging and engaging the percutaneous device from the axial drive mechanism and rotational drive mechanism.

19. The method of claim 15, including;
sensing the axial movement of the percutaneous device and comparing the movement of the axial drive mechanism to determine if the percutaneous device is slipping relative to the axial drive mechanism.

20. The method of claim 19, including;
reducing the speed of a drive motor in the axial drive mechanism until the percutaneous device is no longer slipping relative to the axial drive mechanism.

\* \* \* \* \*